United States Patent

Wang

Patent Number: 5,101,812
Date of Patent: Apr. 7, 1992

[54] ORTHOSIS APPARATUS

[76] Inventor: Tzu C. Wang, 11818 Stallion, Houston, Tex. 77071

[21] Appl. No.: 622,701

[22] Filed: Dec. 3, 1990

Related U.S. Application Data

[63] Continuation-in-part of Ser. No. 401,886, Sep. 1, 1989.

[51] Int. Cl.$^5$ ............................ A61F 5/10; A61F 5/00
[52] U.S. Cl. ........................................ 602/22; 128/878; 128/880; 128/881; 128/882
[58] Field of Search ............... 128/80 R, 77, 80 D, 128/80 F, 80 H, 81 R, 87 R, 87 A, 878, 88 D, 881, 882, 165, 166; 606/53, 54

[56] References Cited

U.S. PATENT DOCUMENTS

| | | | |
|---|---|---|---|
| 3,606,884 | 9/1971 | Peter | 128/80 E |
| 3,698,389 | 10/1972 | Guedel | 128/77 |
| 3,707,963 | 1/1973 | Keropian | 128/77 |
| 3,958,567 | 5/1976 | Callender, Jr. | 128/80 R |
| 4,102,337 | 7/1978 | Golia | 128/80 E |
| 4,103,682 | 8/1978 | Franzl | 128/77 X |
| 4,191,373 | 3/1980 | Lancellotti | 128/77 X |
| 4,289,122 | 9/1981 | Mason et al. | 128/80 E |
| 4,336,796 | 6/1982 | Andrews et al. | 128/87 R |
| 4,554,912 | 11/1985 | Haberman | 128/80 E |
| 4,813,406 | 3/1989 | Ogle, II | 128/77 X |
| 4,886,258 | 12/1989 | Scott | 128/80 R X |

Primary Examiner—Edgar S. Burr
Assistant Examiner—Moshe I. Cohen
Attorney, Agent, or Firm—Henderson & Sturm

[57] ABSTRACT

An improvement in orthosis apparatus (10) for a users limb (100) including a primary support unit (11) operatively and adjustably connected to a secondary support unit (12) by a releasable fastening unit (13), and a body securing unit (14) for captively engaging a selected portion of a users limb (100).

2 Claims, 3 Drawing Sheets

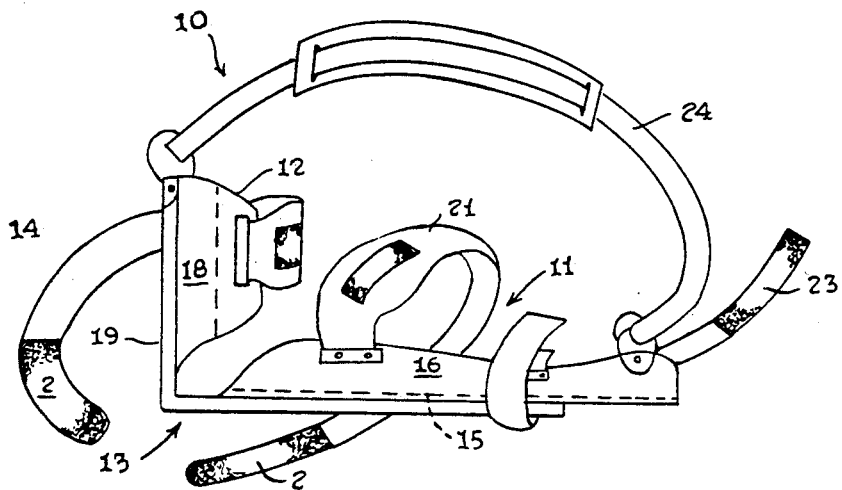
FIG. 4.
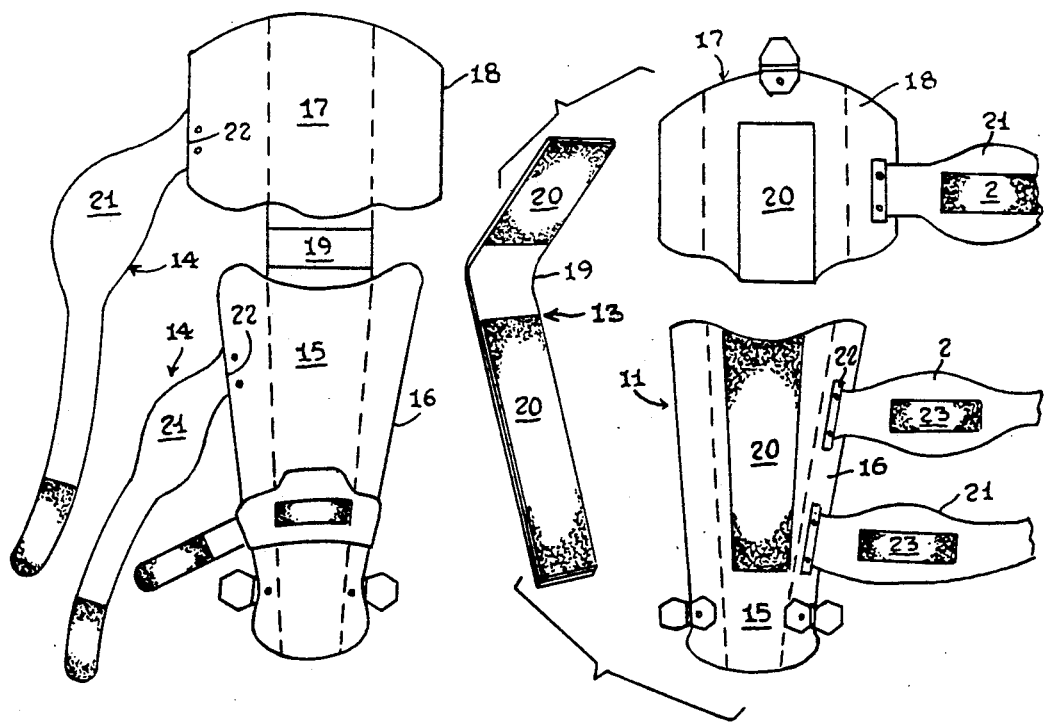
FIG. 5.
FIG. 6.

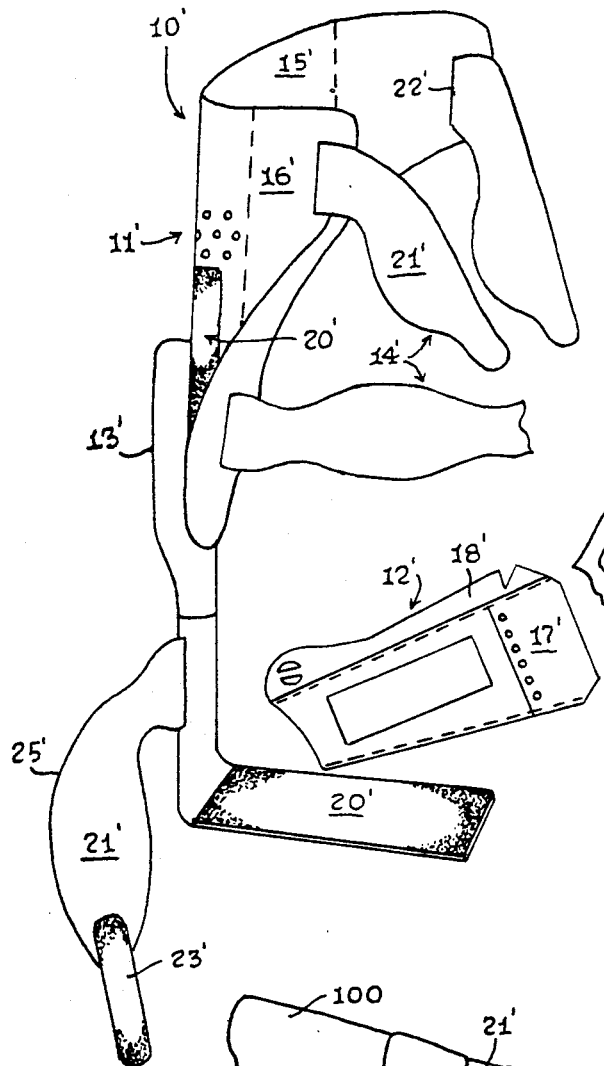
FIG. 7
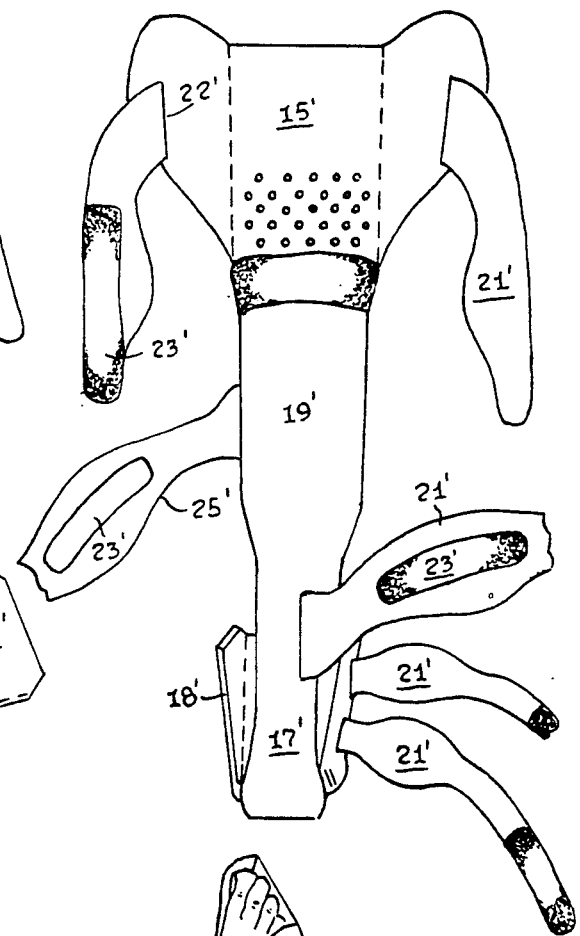
FIG. 8
FIG. 9

ORTHOSIS APPARATUS

BACKGROUND ART

This invention is a continuation in part application of my co-pending patent application Ser. No. 07/401,886 filed on Sept. 1, 1989 and entitled Lower Leg Orthosis Apparatus the content of which is incorporated herein by reference.

As can be seen by reference to the following U.S. Pat. Nos. 3,606,884; 4,289,122; 4,554,912; and 4,102,337; the prior art is replete with myriad and diverse lower leg orthosis apparatus.

While all of the aforementioned prior art constructions are more than adequate for the basic purpose and function for which they have been specifically designed, these devices are likewise limited by the fact that they are specifically concerned with a users leg and foot and are neither designed nor intended for use with other bendable joints such as a persons arm and fingers.

Needless to say until the present time no one has developed a basic orthosis apparatus configuration that can be adapted to a wide variety of uses.

As a consequence of the foregoing situation, there has existed a longstanding need for a family of orthosis apparatus that operate under the same general principles and contain similar structural components; wherein, the family of orthoses apparatus can provide support to the users arms, fingers, and legs; and, the provision of such a construction is a stated objective of the present invention.

DISCLOSURE OF THE INVENTION

Briefly stated, the present invention comprises a variety of orthosis apparatus that share the same basic principals and structural components. To wit the orthosis apparatus that form the basis of the present invention comprise in general; a primary support unit; a secondary support unit; an adjustable fastening unit for connecting the primary support unit to the secondary support unit; and, a body securing unit for operatively attaching the orthosis apparatus to a users body.

As will be explained in greater detail further on in the specification, both the arm and the leg orthosis configurations share virtually identical structural components in that the adjustable fastening unit comprises a generally L-shaped intermediate member which is attached to the primary and secondary support units via hook and loop fasteners which provide the adjustment capability.

BRIEF DESCRIPTION OF THE DRAWINGS

These and other attributes of the invention will become more clear upon a thorough study of the following description of the best mode for carrying out the invention, particularly when reviewed in conjunction with the drawings, wherein:

FIG. 4 is a perspective side view of the arm orthosis;

FIG. 5 is a perspective front view of the arm orthosis;

FIG. 6 is an exploded perspective view of the arm orthosis;

FIG. 7 is a perspective side view of an alternate version of the leg orthosis;

FIG. 8 is a perspective front view of the alternate leg orthosis; and,

FIG. 9 is a side plan view of the alternate leg orthosis in use.

BEST MODE FOR CARRYING OUT THE INVENTION

Figure 2:
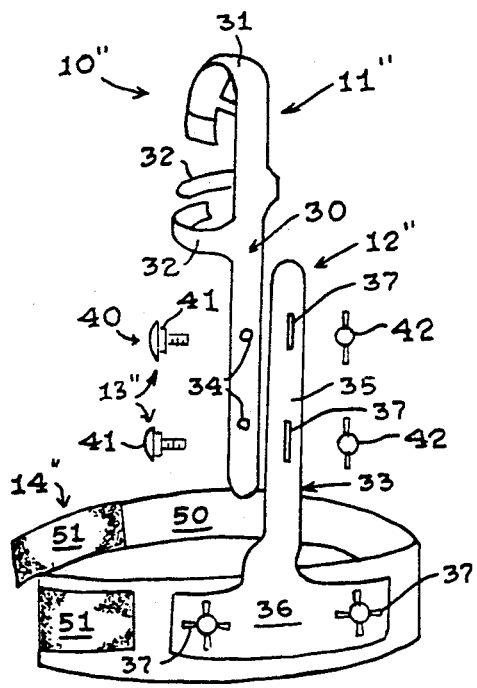
FIG. 2 is an exploded perspective view of the finger orthosis.

As can be seen by reference to the drawings, and in particular to FIGS. 2, 6 and 7, the orthosis apparatus that forms the basis of the present invention is designated generally by the reference numeral (10). The apparatus (10) comprises in general: a primary support unit (11) a secondary support unit (12) a releasable fastening unit (13) and a body securing unit (14). These units will now be described in seriatim fashion.

In as much as the arm orthosis apparatus (10) and the leg orthosis apparatus (10') share virtually identical structural features those apparatus (10)(10') will be described first.

As can best be seen by reference to FIGS. 4 and 6, the arm orthosis apparatus (10) comprises a primary support unit (11) in the form of an elongated generally rigid first support member (15) having curved sides (16) to prevent the lateral displacement of a portion of the users limb (100) such as the forearm. In addition the secondary support unit (12) comprises a relatively short generally rigid second support member (17) having curved sides (18) to likewise limit the lateral displacement of another portion of the users limb, (100) such as the upper arm.

Furthermore the releasable fastening unit (13) comprises an elongated generally rigid and L-shaped intermediate connecting member (19) which is used to operatively connect the primary support unit (11) to the secondary support unit (12).

As mentioned earlier both the arm orthosis apparatus (10) and the leg orthosis apparatus (10') share virtually identical structural components as will be explained presently.

As shown in FIG. 7 the leg orthosis apparatus (10') comprises a primary support unit (11') in the form of an elongated generally rigid first support member (15') having curved sides (16') to prevent the lateral displacement of a portion of the users limb (100) such as the lower leg. In addition the secondary support unit (12') comprises a relatively short generally rigid second support member (17') having raised sides (18') to likewise limit the lateral displacement of another portion of the users limb (100) such as the foot.

Furthermore, the releasable fastening unit (13') comprises an elongated generally rigid and L-shaped intermediate connecting member (19') which is used to operatively connect the primary support unit (11') to the secondary support unit (12').

As can be seen particularly by reference to FIGS. 6 and 7 the releasable fastening units (13) and (13') further comprise hook and loop fasteners (20) (20') which are disposed on the rear surfaces of the primary (11) (11') and surfaces of the intermediate releasable fastening units (13) (13') to join those units together in a well recognized fashion.

As can also be seen by reference to FIGS. 4 through 9, both the primary (11) (11') and the secondary (12) (12') of the arm (10) and leg (10') orthosis apparatus are provided with body securing units (14) (14') in the form of a plurality of elongated strap members (21) (21') which are operatively secured on one end (22)(22') to the first (15) (15') and second (17) (17') support members, furthermore the strap members (21) (21') are further provided with complimentary closure elements (23) (23'), such as hook and loop fasteners; whereby, the strap members (21)(21') may encircle the users limb such as an arms or a leg and be secured upon themselves by the closure elements (23) (23') to captively engage the users limb in a well recognized fashion.

Turning now specifically to FIG. 4 it can be seen that in the arm orthosis apparatus (10) an optional neck strap member (24) is operatively connected between the outboard ends of the first (15) and second (17) support members.

In addition as shown in FIGS. 7 through 9, the releasable fastening unit (13') of the leg orthosis apparatus (10') is further provided with an optional ankle encircling strap member (25') which is secured on one end to the intermediate connecting member (19') and likewise provided with a closure element (23') such that the strap member (25') may captively engage the users ankle in a well recognized fashion.

Figure 1:
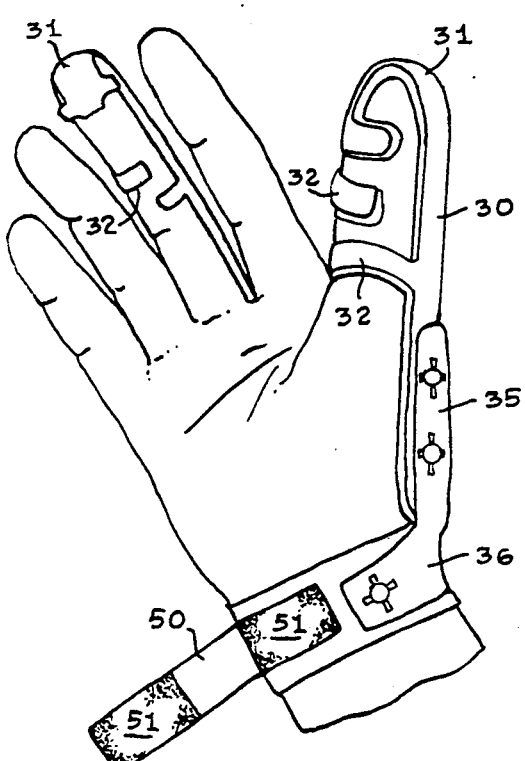
FIG. 1 is a perspective view of the finger orthosis.
Figure 3:
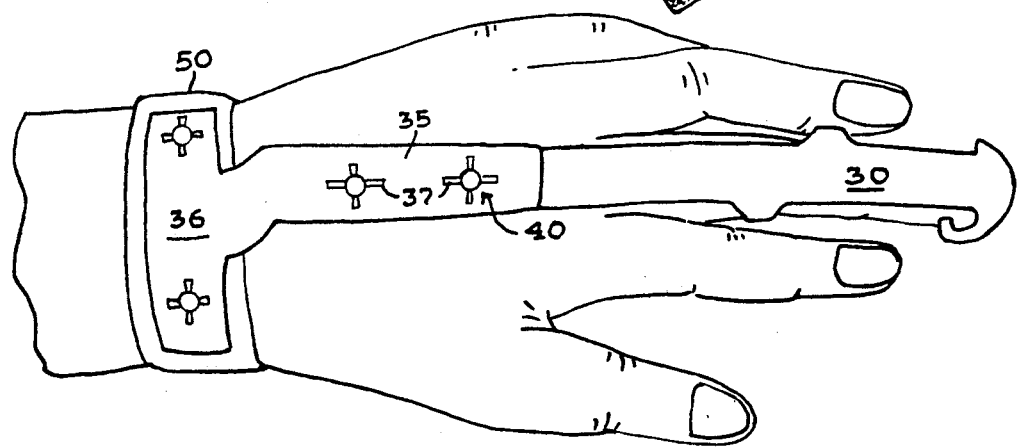
FIG. 3 is a top plan view of the finger orthosis.

As can be seen by reference to FIGS. 1 through 3, the finger and thumb orthosis apparatus (10") represents a structural departure from the other orthosis apparatus (10) and (10'); however, the finger and thumb orthosis apparatus does comprise a primary support unit (11") a secondary support unit (12") a releasable fastening unit (13") and a body securing unit (14").

As shown in FIG. 2, the primary support unit (11") comprises an elongated generally rigid first support member (30) having a curved upper end (31) which is dimensioned to overlap the top of the users digit; and, a pair of offset capture arms (32) which are dimensioned to partially encircle the users digit.

In addition , the secondary support unit (12") comprises a generally rigid inverted T-shaped second support member (33) whose purpose and function will be explained presently.

Still referring to FIG. 2 it can be seen that the first support member (30) is provided with a plurality of discrete apertures (34). In addition both the stem (35) and the cross-member (36) are provided with a plurality of elongated slots (37).

In this version of the preferred embodiment the releasable fastening unit (13") comprises cooperating fastener elements (40) such as a screw (41) and nuts (42) wherein the screws (41) are dimensioned to be received in the discrete apertures (34) in the first support member (30) as well as the slots (37) in the stem (35) of the second support member (33); whereby, the nuts (42) may be engaged with the screws (41) to operatively connect the first support member (30) to the second support member (33) at a desired location.

As can also be seen by reference to FIG. 2 a similar fastening arrangement is employed to operatively connect the second support member (30) to the body securing unit (14"); wherein, the body securing unit (14") comprises an elongated wrist encircling strap element (50) which is further provided with an adjustable closure element (51).

It should further be noted by reference to FIGS. 1 through 3, that a plurality of digit immobilizing orthosis, may be operatively attached to the body securing unit (14") wherein the users fingers as well as their thumb may be selectively immobilized depending on the extent of the users injury.

It should also be appreciated at this juncture that all of the different versions of the releasable fastening units (13) (13') and (13") allow adjustability between the disposition of the primary support units (11) (11') (11") and the secondary support units.

Having thereby described the subject matter of the present invention, it should be apparent that many substitutions, modifications and variations of the invention are possible in light of the above teachings. It is therefore to be understood that the invention as taught and described herein is only to be limited to the extent of the breadth and scope of the appended claims.

I claim:

1. An improvement in orthosis apparatus securable to a selected portion of a persons limbs such as the wrist, arm, and hand; wherein, the orthosis apparatus comprises:

a primary support unit including a first elongated generally rigid support member dimensioned to engage a selected portion of a persons hand and extend along the entire length and around the extremity of a digit on a persons hand;

a secondary support unit including a second generally rigid support member having a generally inverted T-shaped configuration, and dimensioned to engage a selected portion of a persons hand a releasable fastening unit for operatively connecting said first support member to said second support member; and, a wrist securing unit for operatively attaching the orthosis apparatus to the persons wrist; wherein, the wrist securing unit comprises a flexible strap attached to the bottom portion of the second support member; and provided on its ends with cooperating releasable fasteners.

2. The improvement as in claim 1; wherein, said first support member is further provided with a plurality of capture arms which are dimensioned to at least partially encircle said digit.

* * * * *